(12) United States Patent
Leghissa

(10) Patent No.: US 10,765,340 B2
(45) Date of Patent: Sep. 8, 2020

(54) MEDICAL IMAGING DEVICE FOR COMBINED MAGNETIC RESONANCE IMAGING AND IRRADIATION AND METHOD FOR DETERMINING THE CONFIGURATION OF SHIM UNITS

(71) Applicant: Siemens Healthcare GmbH, Erlangen (DE)

(72) Inventor: Martino Leghissa, Wiesenthau (DE)

(73) Assignee: Siemens Healthcare GmbH, Erlangen (DE)

(*) Notice: Subject to any disclaimer, the term of this patent is extended or adjusted under 35 U.S.C. 154(b) by 158 days.

(21) Appl. No.: 16/141,954

(22) Filed: Sep. 25, 2018

(65) Prior Publication Data

US 2019/0090777 A1 Mar. 28, 2019

(30) Foreign Application Priority Data

Sep. 26, 2017 (EP) ..................................... 17193198

(51) Int. Cl.
*G01R 33/565* (2006.01)
*A61B 5/055* (2006.01)
(Continued)

(52) U.S. Cl.
CPC ............ *A61B 5/055* (2013.01); *G01R 33/246* (2013.01); *G01R 33/341* (2013.01);
(Continued)

(58) Field of Classification Search
CPC ............ G01R 33/3804; G01R 33/3806; G01R 33/3808; G01R 33/381; G01R 33/3815;
(Continued)

(56) References Cited

U.S. PATENT DOCUMENTS 8,981,779 B2 3/2015 Shvartsman
2009/0225771 A1 9/2009 Yasuda
(Continued)

FOREIGN PATENT DOCUMENTS

JP 2012533362 A 12/2012
JP 2014519382 A 8/2014
(Continued)

OTHER PUBLICATIONS

Crijns, Sjoerd, and Bas Raaymakers. "From static to dynamic 1.5 T MRI-linac prototype: impact of gantry position related magnetic field variation on image fidelity." Physics in Medicine & Biology 59.13 (2014): 3241.
(Continued)

*Primary Examiner* — Tung X Nguyen
(74) *Attorney, Agent, or Firm* — Lempia Summerfield Katz LLC

(57) ABSTRACT

An imaging system includes a magnetic resonance imaging device and a radiation generator that are mechanically linked to each other such that both surround a patient bore for receiving and positioning the examination subject. The magnetic resonance imaging device has at least one main magnet for generating a magnetic field, and the radiation generator has a radiation source for generating radiation. The imaging system is configured from a static part and a part that is rotatable through an angle of rotation such that at least one rotatable main magnet is rotatable around a static radiation generation unit or a rotatable radiation generation unit is rotatable around at least one static main magnet. The imaging system includes at least two passive shim units, of which at least one static shim unit is stationary and at least one rotatable shim unit is fixedly connected to the rotatable part.

15 Claims, 3 Drawing Sheets

(51) Int. Cl.
*G01R 33/48* (2006.01)
*G01R 33/3873* (2006.01)
*G01R 33/24* (2006.01)
*G01R 33/341* (2006.01)
*G01R 33/561* (2006.01)
*G01R 33/3875* (2006.01)

(52) U.S. Cl.
CPC ..... *G01R 33/3873* (2013.01); *G01R 33/4808* (2013.01); *G01R 33/5611* (2013.01); *G01R 33/5659* (2013.01); *G01R 33/3875* (2013.01); *G01R 33/4812* (2013.01)

(58) Field of Classification Search
CPC G01R 33/383; G01R 33/385; G01R 33/3854; G01R 33/3856; G01R 33/3873; G01R 33/3875
See application file for complete search history.

(56) References Cited

U.S. PATENT DOCUMENTS

| | | | |
|---|---|---|---|
| 2014/0009155 A1* | 1/2014 | Ikezaki | G01R 33/56 324/309 |
| 2014/0043027 A1* | 2/2014 | Overweg | H01R 39/08 324/319 |
| 2014/0084926 A1 | 3/2014 | Amthor | |
| 2015/0247907 A1 | 9/2015 | Heid | |
| 2016/0011288 A1 | 1/2016 | Overweg | |
| 2016/0144200 A1 | 5/2016 | Leach et al. | |
| 2017/0014644 A1 | 1/2017 | Shvartsman et al. | |

FOREIGN PATENT DOCUMENTS

| | | |
|---|---|---|
| JP | 2015500127 A | 1/2015 |
| JP | 2015532844 A | 11/2015 |
| JP | 2016510225 A | 4/2016 |
| JP | 2016526968 A | 7/2017 |
| WO | WO2014121991 A1 | 8/2014 |

OTHER PUBLICATIONS

Wachowicz, K., T. Tadic, and B. G. Fallone. "Geometric distortion and shimming considerations in a rotating MR-linac design due to the influence of low-level external magnetic fields." Medical physics 39.5 (2012): 2659-2668.

European Office Action for European Patent Application No. 17193198.3-1022 dated Aug. 28, 2018.

Wang, Ge, et al. "Vision 20/20: Simultaneous CT-MRI—Next chapter of multimodality imaging." Medical physics 42.10 (2015): 5879-5889.

Wen, Zhifei, et al. "Shimming with permanent magnets for the x-ray detector in a hybrid x-ray/MR system." Medical physics 35.9 (2008): 3895-3902.

Japanese Office Action for Japanese Patent Application No. 2018-177475, dispatched on Sep. 17, 2019, with English translation.

* cited by examiner

MEDICAL IMAGING DEVICE FOR COMBINED MAGNETIC RESONANCE IMAGING AND IRRADIATION AND METHOD FOR DETERMINING THE CONFIGURATION OF SHIM UNITS

This application claims the benefit of EP 17193198.3, filed on Sep. 26, 2017, which is hereby incorporated by reference in its entirety.

BACKGROUND

The present embodiments relate to a medical imaging system for combined magnetic resonance imaging and irradiation of an examination subject, and to a method for determining the configuration of shim units with shim elements.

When a magnetic resonance tomography system is operated in combination with an integrated radiation source (e.g., with an X-ray source or a LINAC (e.g., linear particle accelerator; radiotherapy source), an adjustment of the radiation application angle relative to the patient is desired in most cases for clinical reasons. Either (a) the MR magnet rotates about a longitudinal axis of the MR axis or (b) the remaining components rotate about the static MR magnet. The integrated radiation source is to be able to assume different angulations relative to the examination subject.

In magnetic resonance imaging, a maximally homogeneous magnetic field $B_0$ is to be provided. The field homogeneity is generally in the order of magnitude of a few ppm and lower. Technically, it is not possible to produce magnets with perfect field homogeneity, mainly due to constraints during manufacture, a large number of variables in the manufacturing process, and mechanical and electrical tolerances. In addition, surrounding structures influence the magnetic field and generate field distortions.

In magnet technology, the technique known as shimming is used to compensate for small inhomogeneities that are typically present in magnetic fields, a distinction being made between active and passive shimming. For passive shimming, magnetized material is generally arranged at specific points of the MR scanner during the installation of the magnet. For active shimming, specially manufactured energizable coils (similar to gradient coils) are used. The current flow therethrough may be varied as appropriate in order to fine-tune the homogeneity of the magnetic field.

As a result of the shimming, the field homogeneity within the volume to be visualized is improved in accordance with the desired quality. In passive shimming, ferromagnetic materials (e.g., iron or steel) are arranged in this case in a distributed manner in regular patterns at specific points along the inner bore of the magnet. A typical arrangement for cylindrical superconducting scanners contains between 12 and 24 carrier drawers, known as "trays", that are distributed symmetrically around the circumference of the magnet. Each shim tray is accommodated along the z-axis of the scanner in a type of channel and contains compartments into which a desired number of ferromagnetic shim elements may be inserted.

Known MR imaging systems generally make use of passive and active shimming simultaneously. Active shimming is employed only to shield against low-order (e.g., first- and second-order) field distortion harmonics. Higher orders are suppressed by passive shimming. The advantage of active shimming lies in the ability to make dynamic adjustments to the currents flowing through the coils. This enables the shimming to be modified in order to match the particular examination subject. In present-day MR systems, high-speed automated shimming is routinely performed during the preparatory phase prior to the examination. The disadvantage of passive shimming lies in the fact that passive shimming is a static solution. Changing or replacing the magnet or changing the environment of the magnet typically causes the magnetic field to become more inhomogeneous. As a result, the shimming is also to be adjusted when the magnet rotates about the longitudinal axis of the magnet around an environment of the magnet or when the environment rotates around the static magnet.

In the article "From static to dynamic 1.5 T MRI-linac prototype: impact of gantry position related magnetic field variation on image fidelity," by Sjoerd Crijns and Bas Raaymakers, Phys. Med. Biol. 59, pages 3241-3247, 2014, magnetic field variations of a particle therapy LINAC that rotates on a gantry around a fixed MR magnet are investigated. Field inhomogeneities are reduced in this case by selectively driving the coils for the active shimming in an angle-dependent manner. Only first-order active shims (e.g., linear gradient) are used, while higher-order inhomogeneities are not addressed.

In the article "Geometric distortion and shimming considerations in a rotating MR-linac design due to the influence of low-level external magnetic fields" by K. Wachowicz, T. Tadic and B. G. Fallone, Med. Phys. 39(5), pages 2659-2668, 2012, theoretical solutions for shimming in the case of a rotating MR-LINAC system are discussed. The described solution mentions a passive shim unit that is connected to the rotating magnet and an active shim unit for first- and second-order distortions. Various approaches are examined. For example, a passive shim unit that is optimized for a single angle of rotation or a passive shim unit that offers an average coverage for the entire angular range is provided.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a medical imaging device for combined magnetic resonance imaging and irradiation of an examination subject, in which magnetic field distortions, such as those of a higher order, are shielded with maximum effectiveness, even in arrangements containing some rotating components, is provided. As another example, a method for configuring shim units in order to compensate for magnetic field distortions in arrangements containing some rotating components is provided.

A medical imaging system for combined magnetic resonance imaging and irradiation of an examination subject includes a magnetic resonance imaging unit and a radiation generation unit that are mechanically linked to each other such that the radiation generation unit is structurally integrated with the magnetic resonance imaging unit and both surround a patient bore for receiving and positioning the examination subject. The magnetic resonance imaging unit has at least one main magnet for generating a magnetic field, and the radiation generation unit has a radiation source for generating radiation. The imaging system is embodied from a static part and a part that is rotatable through an angle of rotation such that either at least one rotatable main magnet is arranged so as to be rotatable around a static radiation generation unit or a rotatable radiation generation unit is arranged so as to be rotatable around at least one static main magnet. The imaging system includes at least two passive shim units, of which at least one static shim unit is stationary and at least one rotatable shim unit is fixedly connected to the rotatable part. Magnetic field distortions may be compensated for in an effective manner. In this case, each of the at least two passive shim units handles a portion of the compensation for the magnetic field distortion. A suitable apportioning scheme may therefore achieve an optimal compensation result. The magnetic field distortions as such are originally attributable in part to limitations in the quality of the (e.g., main) magnet and in part to other components of the imaging system or the environment.

According to an embodiment, each of the at least two passive shim units has a plurality of shim elements, and the shim elements are arranged and distributed in the shim units such that the shim elements compensate at least to some degree (e.g., by at least 95%) for magnetic field distortions.

For example, the two passive shim units are embodied to compensate for magnetic field distortions of at least the second order and/or a higher order.

According to an embodiment, the at least one static shim unit is configured to compensate at least to some degree for a first magnetic field distortion component that is not dependent on the angle of rotation, and the at least one rotatable shim unit is configured to compensate at least to some degree for a second magnetic field distortion component that is dependent on the angle of rotation. Apportioning the magnetic field distortions to be compensated for in such a way into rotation-angle-dependent and -independent magnetic field distortions and compensating therefor by the corresponding shim unit provides a particularly homogeneous magnetic field $B_0$ as result. This makes it possible to achieve particularly high-quality MR imaging.

According to an embodiment, the radiation generation unit is formed by an X-ray imaging unit, and the X-ray imaging unit includes an X-ray source for generating an X-ray beam. Combined magnetic resonance imaging and X-ray imaging devices are particularly suitable for providing a comprehensive and complementary visualization of bones, organs, and tissue that may be used for diagnosing the widest range of disorders. The X-ray imaging unit also includes an X-ray detector for converting radiation into image data.

At least one active shim unit including a plurality of coils may also be provided to compensate for further magnetic field distortions of particularly low order. The plurality of coils being are configured as selectively controllable with respect to the energizing current flowing therethrough, In one embodiment, a method for determining the configuration of shim units with shim elements in the case of an above-cited medical imaging system is provided. The method includes measuring the field distribution of the magnetic field of the magnetic resonance imaging unit (e.g., inside the patient bore) as a function of the angle of rotation, and determining the magnetic field distortion therefrom. The method also includes determining a first magnetic field distortion component that is not dependent on the angle of rotation, and a second component that is dependent on the angle of rotation. The method includes determining the distribution of shim elements in the static shim unit in order to compensate for the first magnetic field distortion component, and determining the distribution of shim elements in the rotatable shim unit in order to compensate for the second magnetic field distortion component. For example, the number, size, and position of the shim elements in the shim units are determined or calculated in order to enable the configuration process to be carried out subsequently in a simple manner.

According to a further embodiment, the shim elements are inserted into the shim units in accordance with the calculated distribution. This may be carried out manually (e.g., by a service engineer) or automatically by a shimming tool. Subsequently, by repeating the measurement of the field distribution of the magnetic field, it may be checked whether the compensation is sufficient, and possibly a further calculation and a further configuration process may be carried out.

DETAILED DESCRIPTION

The present embodiments are described in the following figures with reference to a medical imaging system including a rotating main magnet of the magnetic resonance imaging unit and a static X-ray imaging unit; alternatively, the magnetic resonance imaging unit may be static, and the X-ray imaging unit may be rotatable.

Figure 1:
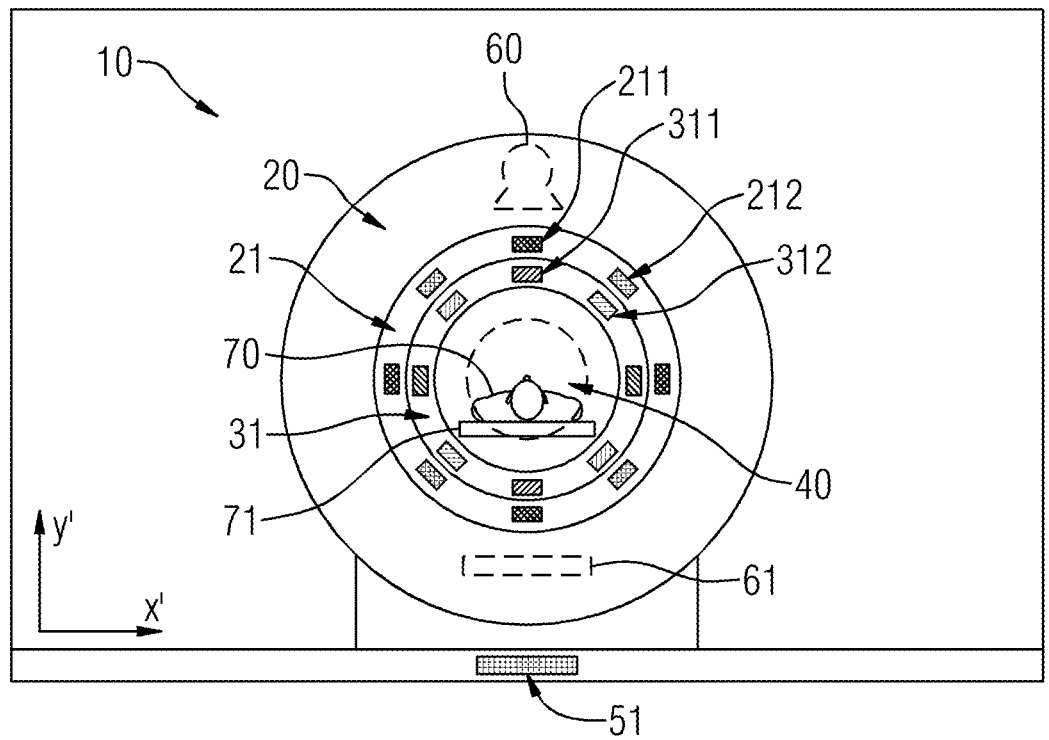
FIG. 1 shows a view of one embodiment of an imaging system including two passive shim units.

FIG. 1 shows a medical imaging system 10 that includes a magnetic resonance imaging unit (e.g., a magnetic resonance imaging device) having a main magnet 20 rotating around a bore 40, as well as a static X-ray imaging unit (e.g., an X-ray imaging device) having an X-ray source 60 and an X-ray detector 61. The imaging system 10 also includes a passive shim unit 21 that is rotatable with the rotatable main magnet 20, and a static passive shim unit 31. In this arrangement, the rotatable passive shim unit 21 may be structurally linked to the main magnet 20 such that the rotatable passive shim unit 21 automatically co-rotates correspondingly with the main magnet 20 during a rotation of the main magnet 20. The magnetic resonance imaging unit and the X-ray imaging unit surround the patient bore 40, in which a patient table 71, with a patient 70 (e.g., the examination subject, such as a part/organ of the patient) positioned and supported thereon, is arranged.

The two passive shim units (e.g., the rotatable passive shim unit 21 and the static passive shim unit 31) are configured to compensate for magnetic field distortions of the magnetic field as a whole. The magnetic field distortions are caused in part by quality limitations of the main magnet, by magnetic components of the imaging system, and by magnetic elements 51 of the environment of the imaging system. For compensation purposes, each shim unit has a plurality of shim trays containing pockets. The pockets may be populated with a plurality of shim elements (e.g., plates)

made of ferromagnetic sheet iron. The shim elements are arranged in the pockets of the shim trays such that the shim elements are able to compensate for the magnetic field distortions. In the view shown, the rotatable shim unit 21 has a first shim tray 211 and a second shim tray 212, as well as six further shim trays, while the static shim unit 31 has a first shim tray 311, a second shim tray 312, and six further shim trays. In this case, the number of eight shim trays in each case is simply by way of example. As another example, 12 to 24 or even more shim trays may be provided. Prior to commissioning of the magnetic resonance imaging unit, the appropriate number of shim elements are inserted as required into the shim trays in order to compensate, at least to some degree (e.g., by at least 50% to 95%), for magnetic field distortions (e.g., magnetic field distortions of a higher order, such as greater than first order).

Figure 2:
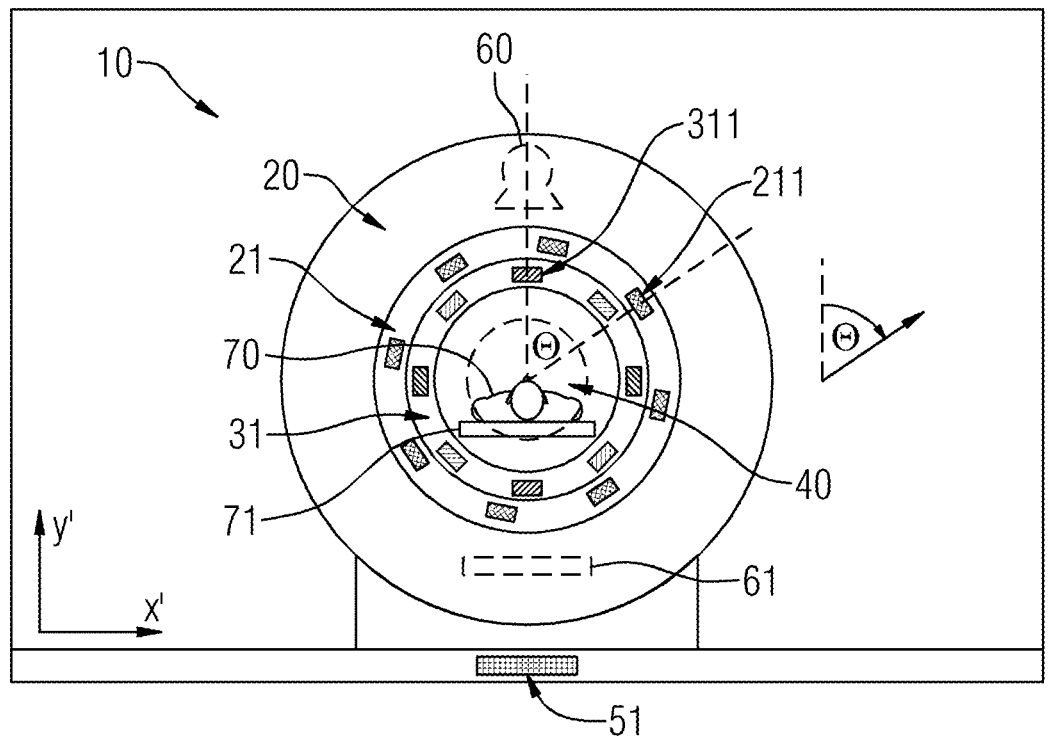
FIG. 2 shows a view of the imaging system according to FIG. 1 including a main magnet rotated through an angle of rotation Θ.

FIG. 2 shows the medical imaging system for the scenario in which the main magnet 20 has been rotated through an angle of rotation Θ. In this case, the rotatable passive shim unit 21 likewise rotates through the angle of rotation Θ around the center of rotation (e.g., the center point of the patient bore 40), while the position of the static passive shim unit 31 does not change. The coordinate system of the static reference system (e.g., static part of the imaging system) has the coordinates x', y' and z' in this case.

When being populated with shim elements, the static passive shim unit 31 is configured to compensate at least to some degree for a first component of the magnetic field distortion. The first component of the magnetic field distortion is not dependent on an angle of rotation. The static passive shim unit 31 compensates for the angle-independent component of the magnetic field distortion by at least 50% to 95%. The static passive shim unit therefore compensates for the magnetic field distortion components that are caused by the static parts of the imaging system and by the environment. When being populated with shim elements, the rotatable passive shim unit 21 is configured to compensate at least to some degree for a second component of the magnetic field distortion of the main magnet. The second component of the magnetic field distortion is dependent on an angle of rotation. In one embodiment, the rotatable passive shim unit 21 compensates by at least 95% for the angle-dependent component of the magnetic field distortion. The rotatable passive shim unit therefore compensates for the magnetic field distortion components that are caused by the rotatable main magnet and other rotatable parts of the imaging system.

Figure 4:
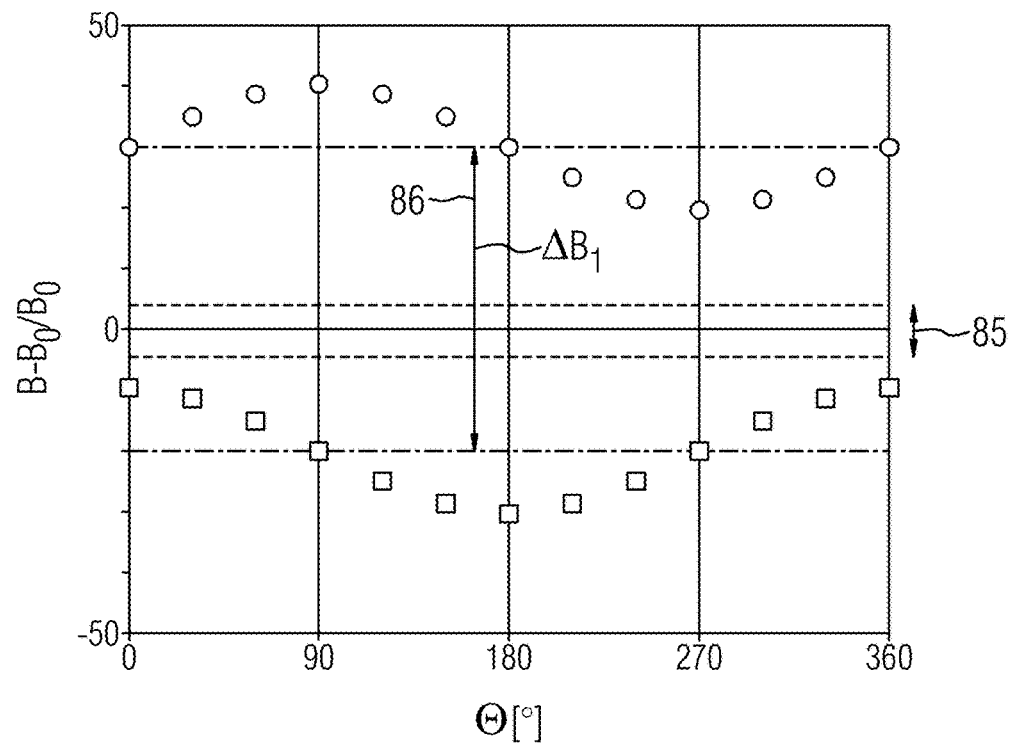
FIG. 4 shows an exemplary measurement of a magnetic field distortion as a function of the angle of rotation prior to shimming.
Figure 5:
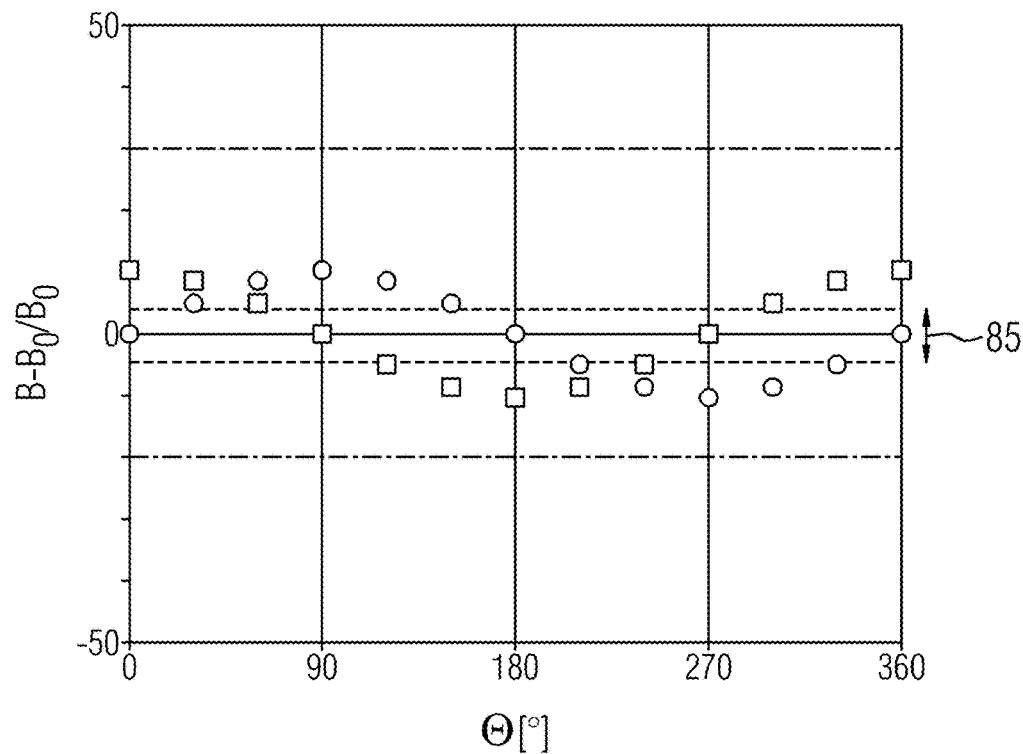
FIG. 5 shows an exemplary measurement of a magnetic field distortion as a function of the angle of rotation after shimming by a passive static shim unit.
Figure 6:
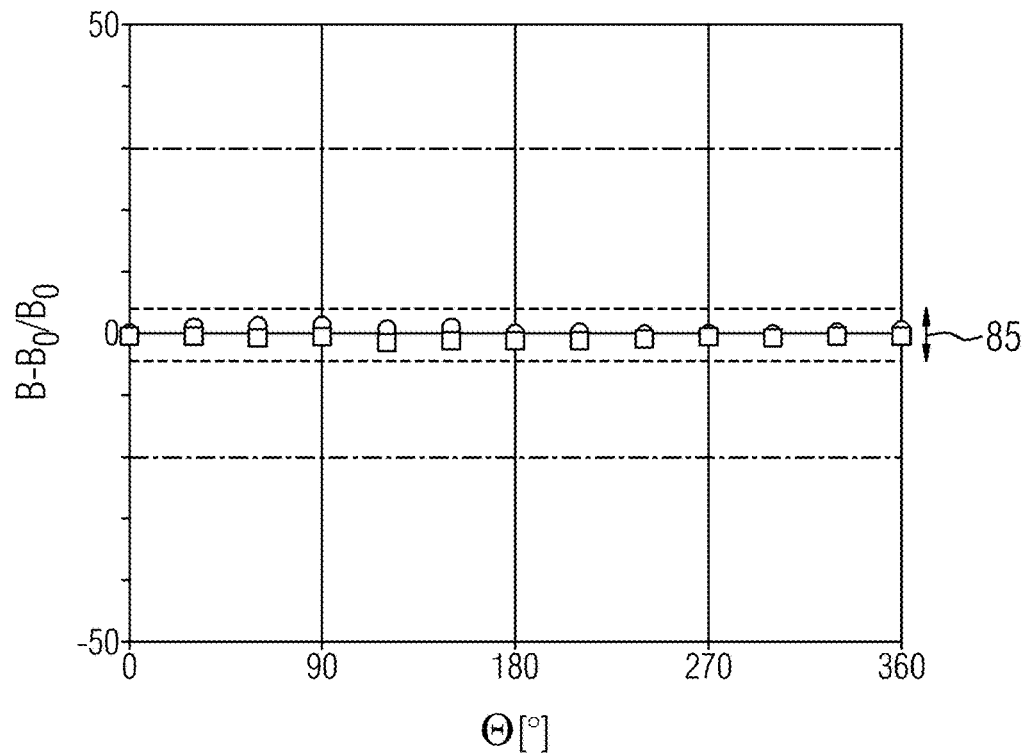
FIG. 6 shows an exemplary measurement of a magnetic field distortion as a function of the angle of rotation after shimming by a passive static shim unit and a passive rotating shim unit.

This may be illustrated, for example, with reference to FIGS. 4 to 6. In FIG. 4, the entire, as yet uncompensated, measured magnetic field distortion $$\frac{B - B_0}{B_0}$$

for two arbitrarily chosen points inside the patient bore is plotted against the angle of rotation Θ (e.g., from 0° to 360°) of the rotatable parts of the imaging system. B is the real magnetic field in this case, and $B_0$ is the desired magnetic field without magnetic field distortion. The targeted threshold value 85 for the magnetic field distortion following compensation in this case amounts to, for example, 5% of the original magnetic field distortion. The angle-independent first component 86 of the magnetic field distortion is indicated by an arrow. If the static passive shim unit 31 is populated so as to compensate (e.g., by 95%) for the angle-independent first component of the magnetic field distortion, in a subsequent measurement, as shown in FIG. 5 (likewise measured magnetic field distortion $$\frac{B - B_0}{B_0}$$

for the same two points as in FIG. 4, plotted against the angle of rotation Θ of the rotatable parts of the imaging system), only the angle-dependent component of the magnetic field distortion is still present. If the component is subsequently compensated for by the configuration of the rotatable passive shim unit 21, then, when the magnetic field distortion is remeasured, a diagram as shown in FIG. 6, in which the remainder of the magnetic field distortion reaches only the targeted threshold value 85 at a maximum, is yielded.

Figure 3:
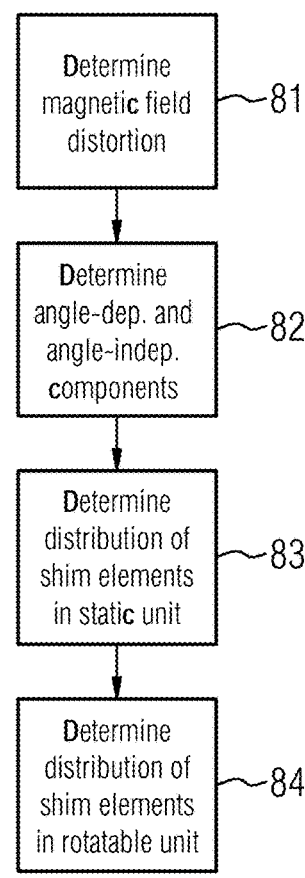
FIG. 3 shows a process flow sequence of one embodiment of a method for determining a configuration of shim units.

FIG. 3 shows a process flow sequence of one embodiment of a method for configuring shim units with shim elements in a medical imaging system. In act 81, a field distribution ΔB(x',y',z',Θ) of a magnetic field of a magnetic resonance imaging unit is measured inside a patient bore of a main magnet as a function of an angle of rotation Θ, and the corresponding distribution of the magnetic field distortion is determined therefrom. The "mapping" of the field distribution and determining of the magnetic field distortion are generally known. In the present case, attention is focused, for example, on the angular dependence (e.g., the rotatable parts of the magnetic resonance imaging unit are rotated, and at the same time, measurements are carried out at a plurality of angles of rotation for a plurality of points inside the patient bore). In act 82, the magnetic field distortion is subdivided into a first magnetic field distortion component (e.g., a first component) and a second magnetic field distortion component (e.g., a second component). The first component is not dependent on the angle of rotation. The second component is dependent on the angle of rotation. The first component and second component may be calculated by a calculation unit (e.g., one or more processors) by applying an algorithm as follows:

$$\Delta B(x',y',z',\Theta) = \Delta B_1(x',y',Z) + \Delta B_2(x',y',z',\Theta)$$

where $B_1$ is the first rotation-angle-independent component, and $B_2$ is the second rotation-angle-dependent component of the magnetic field distortion. In this case, x', y' and z' are the spatial coordinates in the non-rotating reference system (e.g., in the part of the imaging system that is static).

Act 83 and act 84 may also be performed in an altered sequence. In act 83, the distribution of the shim elements in the static shim unit 31 is determined or calculated for the purpose of compensating for the first magnetic field distortion component (e.g., to establish which shim elements are to be placed into which shim trays of the static shim unit in order to achieve a compensation for the first magnetic field distortion component). In act 84, the distribution of the shim elements in the rotatable shim unit 21 is determined or calculated for the purpose of compensating for the second (e.g., angle-dependent) magnetic field distortion component (e.g., to establish which shim elements are to be placed into which shim trays of the rotatable shim unit in order to achieve a compensation for the second magnetic field distortion component). For example, the number, size, and position of the shim elements in the shim units are determined or calculated in order to enable the configuring process to be carried out subsequently in a simple manner.

According to a further embodiment, the shim elements are inserted into the shim units in accordance with the calculated distribution. This may be carried out manually (e.g., by a service engineer or else automatically by a shimming tool). Subsequently, by repeating the measurement of the field distribution of the magnetic field, it may be checked whether the compensation is sufficient, and possibly, a further calculation and a further configuration, or, iteratively, a plurality of calculations and configurations, may be carried out. Alternatively, after the third act 83, a configuration of the corresponding shim unit and remeasurement of the magnetic field distortion may take place, and only then, the calculation of the configuration of the second passive shim unit may be performed.

For the embodiment in which an imaging system includes a static main magnet and a rotatable gantry with an X-ray imaging unit, the rotatable passive shim unit co-rotates with the gantry around the main magnet, while the static passive shim unit remains fixed in position. In this case too, in the same way as described above, the magnetic field distortion components that are to be compensated for are subdivided into rotation-angle-dependent and rotation-angle-independent components.

Alternatively, a different radiation generation unit (e.g., a LINAC) may also be provided instead of an X-ray imaging unit.

In addition to the passive shim units 21, 31, one or more active shim units (not shown) may also be provided. An active shim unit may include selectively controllable coils that may be flexibly switched at any time such that the selectively controllable coils compensate for corresponding magnetic field distortion components that have not yet been compensated for. The active shim unit is used, for example, to compensate for the remnant magnetic field distortion (e.g., 5%), for a time-varying magnetic field distortion component, or for the zero- or first-order magnetic field distortion. The active shim unit may be selectively controlled (e.g., in an angle-dependent manner).

In order to improve the field homogeneity of the magnetic field also in relation to higher-order distortions and in relation to all angles of rotation, the following is provided: A medical imaging system for combined magnetic resonance imaging and irradiation of an examination subject that includes a magnetic resonance imaging unit and a radiation generation unit that are mechanically linked to each other such that the radiation generation unit is structurally integrated with the magnetic resonance imaging unit and both surround a patient bore for receiving and positioning the examination subject. The magnetic resonance imaging unit has at least one main magnet for generating a magnetic field, and the radiation generation unit has a radiation source for generating radiation. The imaging system is embodied from a static part and a part that is rotatable through an angle of rotation such that either at least one rotatable main magnet is arranged so as to be rotatable around a static radiation generation unit, or a rotatable radiation generation unit is arranged so as to be rotatable around at least one static main magnet. The imaging system includes at least two passive shim units, of which at least one static shim unit is stationary and at least one rotatable shim unit is fixedly connected to the rotatable part.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A medical imaging system for combined magnetic resonance imaging and irradiation of an examination subject, the medical imaging system comprising:
   a magnetic resonance imaging device and a radiation generator that are mechanically linked to each other such that the radiation generator is structurally integrated with the magnetic resonance imaging device and the magnetic resonance imaging device and the radiation generator surround a patient bore for receiving and positioning the examination subject, wherein the magnetic resonance imaging device includes at least one main magnet operable to generate a magnetic field, and the radiation generator includes a radiation source operable to generate radiation, wherein one of the magnetic resonance imaging device and the radiation generator includes a static part and the other of the magnetic resonance imaging device and the radiation generator includes a rotatable part that is rotatable through an angle of rotation, wherein the rotatable part includes one or more main magnets of the at least one main magnet that are rotatable and are arranged so as to be rotatable around the static part, which includes the radiation generator, or the rotatable part includes the radiation generator and is arranged so as to be rotatable around the static part, which includes one or more main magnets of the at least one main magnet that are static; and
   at least two passive shim units, wherein at least one passive shim unit of the at least two passive shim units is a static shim unit that is stationary, and at least one passive shim unit of the at least two passive shim units is a rotatable shim unit that is fixedly connected to the rotatable part.

2. The medical imaging system of claim 1, wherein each passive shim unit of the at least two passive shim units includes a plurality of shim elements, and
   wherein the plurality of shim elements are arranged in the respective passive shim unit such that the plurality of shim elements compensate for magnetic field distortions at least to some degree.

3. The medical imaging system of claim 2, wherein the plurality of shim elements are arranged in the respective passive shim unit such that the plurality of shim elements compensate for magnetic field distortions by at least 95%.

4. The medical imaging system of claim 2, wherein the magnetic field distortions that are to be compensated for are of the second order, one or more orders higher than second order, or any combination thereof.

5. The medical imaging system of claim 1, wherein the at least one static shim unit is configured to compensate, at least to some degree, for a first magnetic field distortion component that is not dependent on the angle of rotation, and the at least one rotatable shim unit is configured to compensate, at least to some degree, for a second magnetic field distortion component that is dependent on the angle of rotation.

6. The medical imaging system of claim 5, wherein the at least one static shim unit is configured to compensate for the first magnetic field distortion component by at least 95%, and the at least one rotatable shim unit is configured to compensate for the second magnetic field distortion component by at least 95%.

7. The medical imaging system of claim 1, wherein the radiation generator includes an X-ray imaging unit, and the X-ray imaging unit includes an X-ray source for generating an X-ray beam.

8. The medical imaging system of claim 5, wherein the X-ray imaging unit also includes an X-ray detector for converting radiation into image data.

9. The medical imaging system of claim 1, further comprising at least one active shim unit, the at least one active shim unit including a plurality of coils,
wherein the plurality of coils are configured as selectively controllable with respect to an energizing current flowing through the plurality of coils.

10. A method for determining a configuration of shim units with shim elements in a medical imaging system, the method comprising:
measuring a field distribution of a magnetic field of a magnetic resonance imaging device of the medical imaging system as a function of an angle of rotation of a rotatable part, the rotatable part including at least one main magnet of the magnetic resonance imaging device or a radiation generator of the medical imaging system;
determining a magnetic field distortion from the measured field distribution;
determining a first magnetic field distortion component that is not dependent on the angle of rotation of the rotatable part, and a second magnetic field distortion component that is dependent on the angle of rotation of the rotatable part; and
determining a distribution of shim elements in a static shim unit of the shim units for compensation for the first magnetic field distortion component; and
determining a distribution of shim elements in a rotatable shim unit of the shim units for compensation for the second magnetic field distortion component.

11. The method of claim 10, wherein the magnetic resonance imaging device and the radiation generator are mechanically linked to each other such that the radiation generator is structurally integrated with the magnetic resonance imaging device and the magnetic resonance imaging device and the radiation generator surround a patient bore for receiving and positioning an examination subject, and
wherein measuring the field distribution of the magnetic field of the magnetic resonance imaging device comprises measuring a field distribution of a magnetic field inside the patient bore.

12. The method of claim 10, further comprising determining or calculating a number, a size, and a position of the shim elements in the shim units.

13. The method of claim 10, further comprising inserting the shim elements into the shim units in accordance with the determined distribution of shim elements in the static shim unit and the determined distribution of shim elements in the rotatable shim unit.

14. The method of claim 11, further comprising inserting the shim elements into the shim units in accordance with the determined distribution of shim elements in the static shim unit and the determined distribution of shim elements in the rotatable shim unit.

15. The method of claim 12, further comprising inserting the shim elements into the shim units in accordance with the determined distribution of shim elements in the static shim unit and the determined distribution of shim elements in the rotatable shim unit.

* * * * *